United States Patent
Leysieffer et al.

(10) Patent No.: US 6,398,717 B1
(45) Date of Patent: Jun. 4, 2002

(54) DEVICE FOR MECHANICAL COUPLING OF AN ELECTROMECHANICAL HEARING AID CONVERTER WHICH CAN BE IMPLANTED IN A MASTOID CAVITY

(75) Inventors: Hans Leysieffer, Taufkirchen; Gerd M. Müller, Lohhof, both of (DE)

(73) Assignee: Phonak AG, Stafa (CH)

( * ) Notice: Subject to any disclaimer, the term of this patent is extended or adjusted under 35 U.S.C. 154(b) by 0 days.

(21) Appl. No.: 09/576,009

(22) Filed: May 22, 2000

(30) Foreign Application Priority Data

May 21, 1999 (DE) .......................... 199 23 403

(51) Int. Cl.$^7$ .............................................. H04R 25/00
(52) U.S. Cl. ......................................................... 600/25
(58) Field of Search .............................. 600/25; 607/55, 607/56, 57; 623/10

(56) References Cited

U.S. PATENT DOCUMENTS

| | | |
|---|---|---|
| 3,712,962 A | 1/1973 | Epley |
| 3,870,832 A | 3/1975 | Fredrickson |
| 3,882,285 A | 5/1975 | Nunley et al. |

(List continued on next page.)

FOREIGN PATENT DOCUMENTS

| | | |
|---|---|---|
| DE | 197 45 331 | 4/1999 |
| EP | 0 556 300 | 8/1993 |
| WO | WO 90/11737 | 10/1990 |
| WO | WO 98/06235 | 2/1998 |
| WO | WO 98/06236 | 2/1998 |
| WO | WO 98/06237 | 2/1998 |
| WO | WO 98/06238 | 2/1998 |

OTHER PUBLICATIONS

H. Leysieffer et al., Ein Vollständig Implantierbares Hoörsystem für Innenohrschwerhörige: TICA LZ 3001, HNO 1998, vol. 46, Oct. 1998, pp. 853–863.

H.P. Zenner et al., Erste Implantationen Eines Vollständig Implantierbaren Elektronischen Hörsystems Bei Patienten Mit Innenohr–Schwerhörigkeit, HNO 1998, vol. 46, Oct. 1998, pp. 844–852.

Anthony J. Maniglia et al., Contactless Semi–Imlantable Electromagnetic Middle Ear Device for the Treatment of Sensorineural Hearing Loss, vol. 28, No. 1, Feb. 1995, pp. 121–141.

(List continued on next page.)

*Primary Examiner*—Kevin Shaver
*Assistant Examiner*—Brian Szmal
(74) *Attorney, Agent, or Firm*—Nixon Peabody LLP; David S. Safran

(57) ABSTRACT

Device for mechanical coupling of an output-side converter part (15) of an electromechanical hearing aid converter (13), which can be implanted in an artificial mastoid cavity outside the region of the middle ear, the converter part having a capacity to be excited to mechanical vibrations, to a preselected coupling site (16) on one of the ossicular chain, the footplate of the stapes, the membrane which closes the round window, or an artificial window in the cochlea, in the vestibulum or in the labyrinth (equilibrium organ), the device comprising a biocompatible, mechanically passive coupling arrangement (17) which is connected to the output-side converter part and which reaches in the implanted state from the mastoid cavity into the tympanic cavity and adjoins the coupling site with the coupling end (18). The coupling end (18) of a coupling element (22, 29, 34, 37, 40, 46, 52, 59, 68, 71, 77, 81, 88, 95) is formed with a contact surface (32) which has a surface shape which is matched or which can be matched to the surface shape of the coupling site and has a surface composition and surface size such that by placing the coupling end against the coupling site dynamic tension-compression force coupling of the coupling element and the preselected coupling site occurs by surface adhesion which is sufficient for reliable mutual connection of the coupling element and the coupling site.

18 Claims, 7 Drawing Sheets

U.S. PATENT DOCUMENTS

| | | | |
|---|---|---|---|
| 4,850,962 A | | 7/1989 | Schaefer |
| 5,015,224 A | | 5/1991 | Maniglia |
| 5,015,225 A | | 5/1991 | Hough et al. |
| 5,061,280 A | * | 10/1991 | Prescott ..................... 623/10 |
| 5,277,694 A | | 1/1994 | Leysieffer et al. |
| 5,279,292 A | | 1/1994 | Baumann et al. |
| 5,554,096 A | | 9/1996 | Ball |
| 5,624,376 A | | 4/1997 | Ball et al. |
| 5,707,338 A | | 1/1998 | Adams et al. |
| 5,788,711 A | | 8/1998 | Lehner et al. |
| 5,941,814 A | | 8/1999 | Lehner et al. |
| 6,099,462 A | * | 8/2000 | aWengen ..................... 600/25 |

OTHER PUBLICATIONS

John M. Fredrickson et al., Ongoing Investigations into an Implantable Electromagnetic Hearing Aid for Moderate to Severe Sensorineural Hearing Loss, vol. 28, No. 1, Feb. 1995, pp. 107–121.

Naoki Yanagihara et al., Efficacy of the Partially Implantable Middle Ear Implant in Middle and Inner Ear Disorders, Adv. Audiol., vol. 4, Karger, Basel 1988, pp. 149–159.

Jun–Ichi Suzuki et al., Implantation of Partially Implantable Middle Ear Implant and the Indication, Adv. Audiol., vol. 4, Karger, Basel 1988, pp. 160–166.

J.–I. Suzuki, Middle Ear Implant: Implantable Hearing Aids, Advances in Audiology, vol. 4, Apr. 1999, p. 10.

H.P. Zenner, et al., Active Electronic Hearing Implants for Labyrinthine and Conduction Deafness—A New Era of Ear Surgery, HNO 1997—vol. 45, Oct. 1997, pp. 749–774.

H. Leysieffer et al., An Implantable Piezoelectric Hearing Aid Converter for Patients with Labyrinthine Deafness, HNO 1997—vol. 45, Oct. 1997, pp. 792–800.

R. Lehner et al., Cold–Flowing Elements for Coupling of an Implantable Hearing Aid Converter to Auditory Ossicle or Perilymph, HNO 1998—vol. 46, Jan. 1998, pp. 27–37.

* cited by examiner

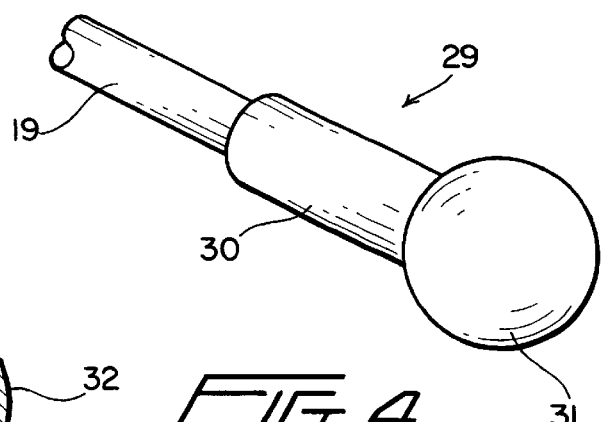
FIG. 4
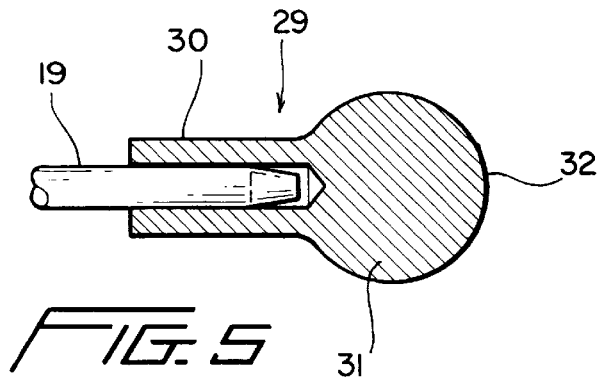
FIG. 5
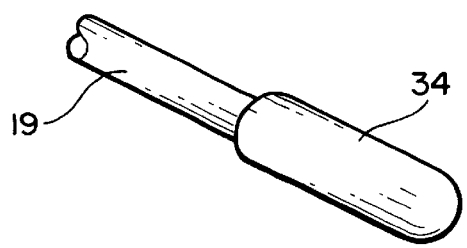
FIG. 6
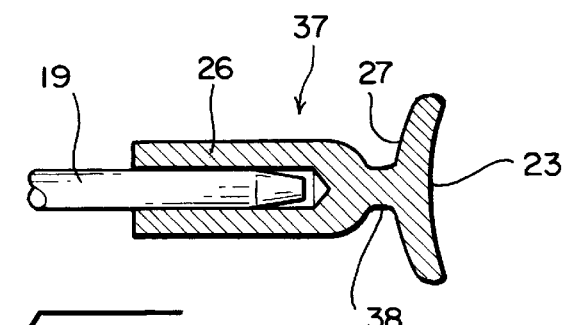
FIG. 7
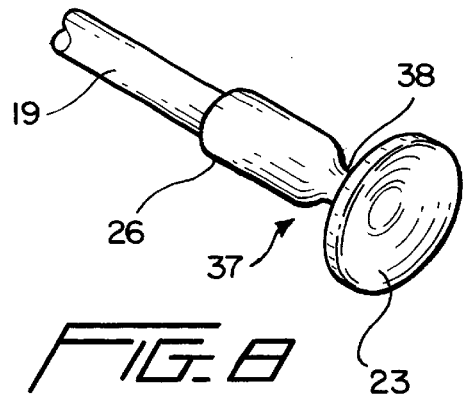
FIG. 8
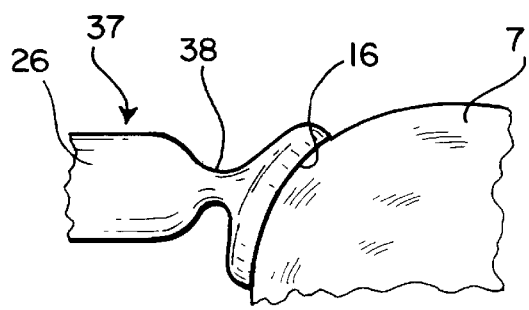
FIG. 9
FIG. 10

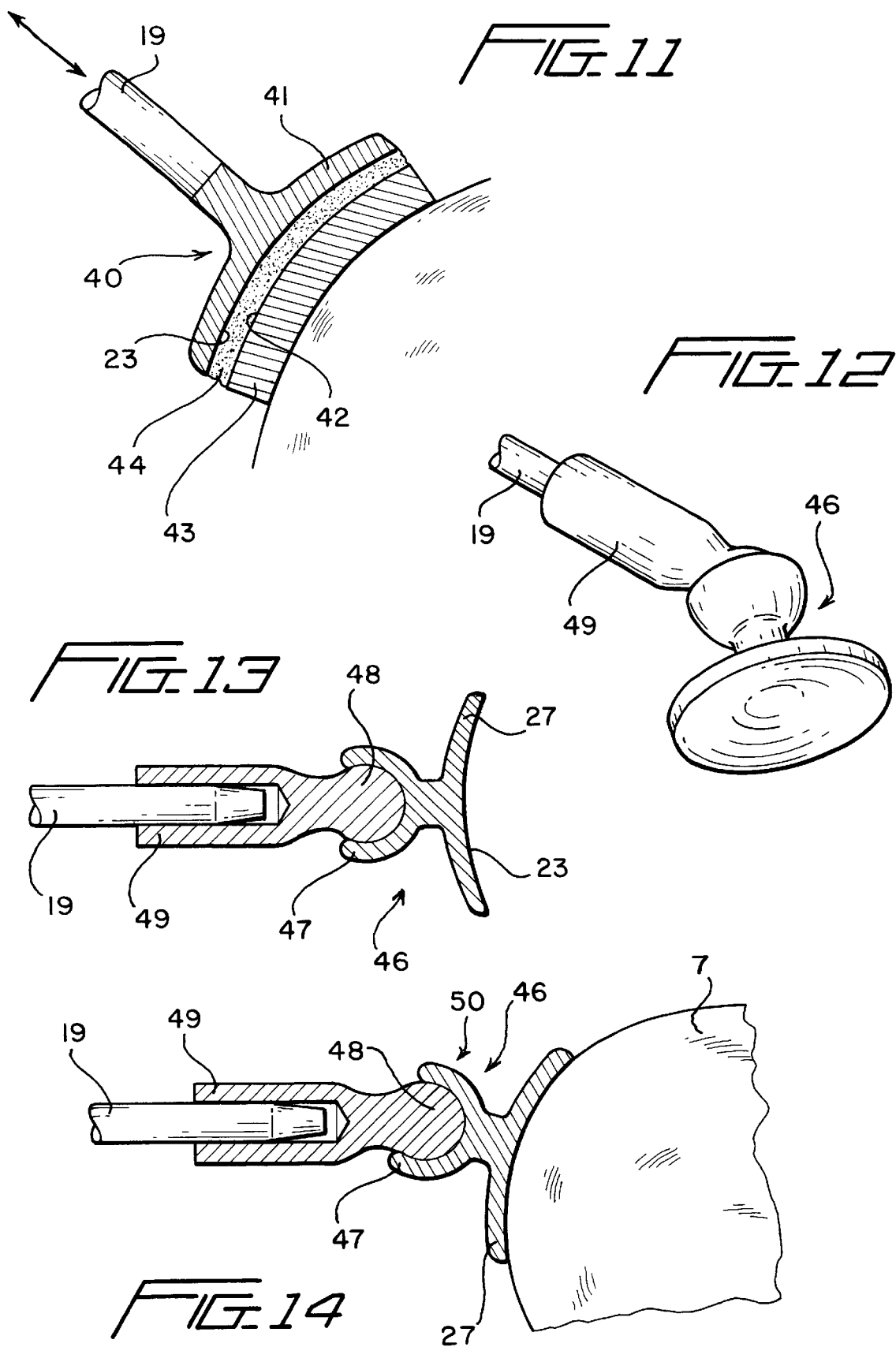

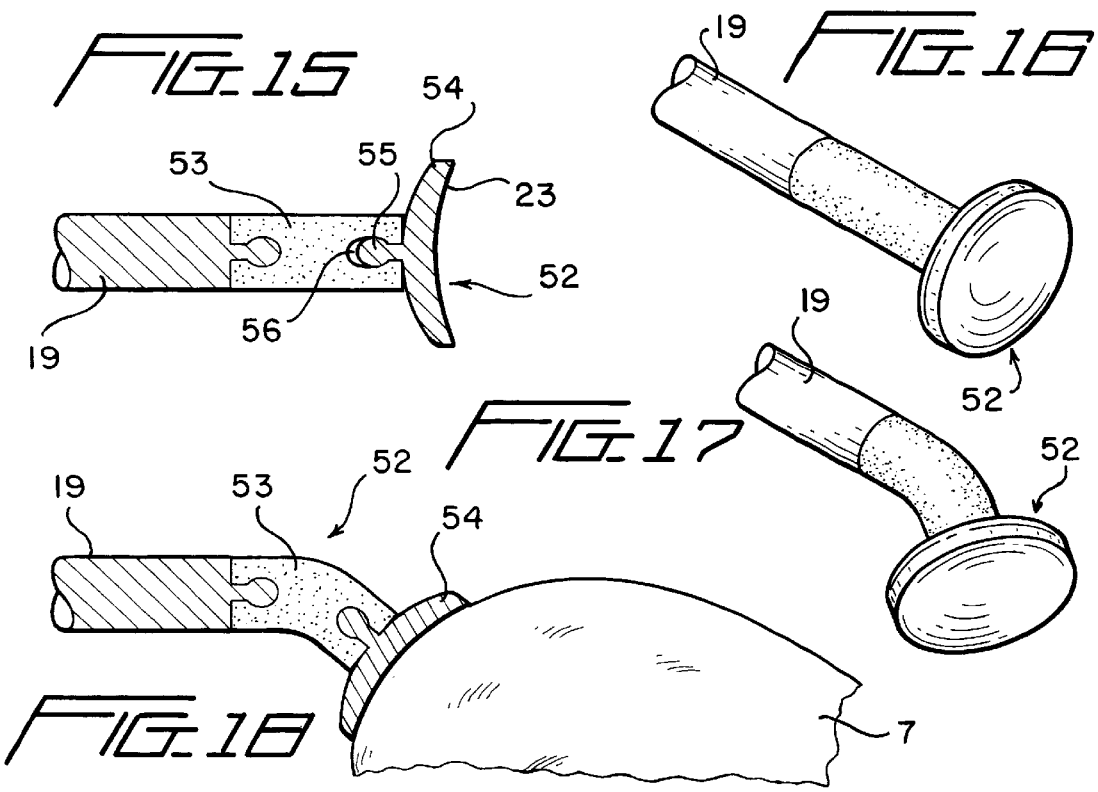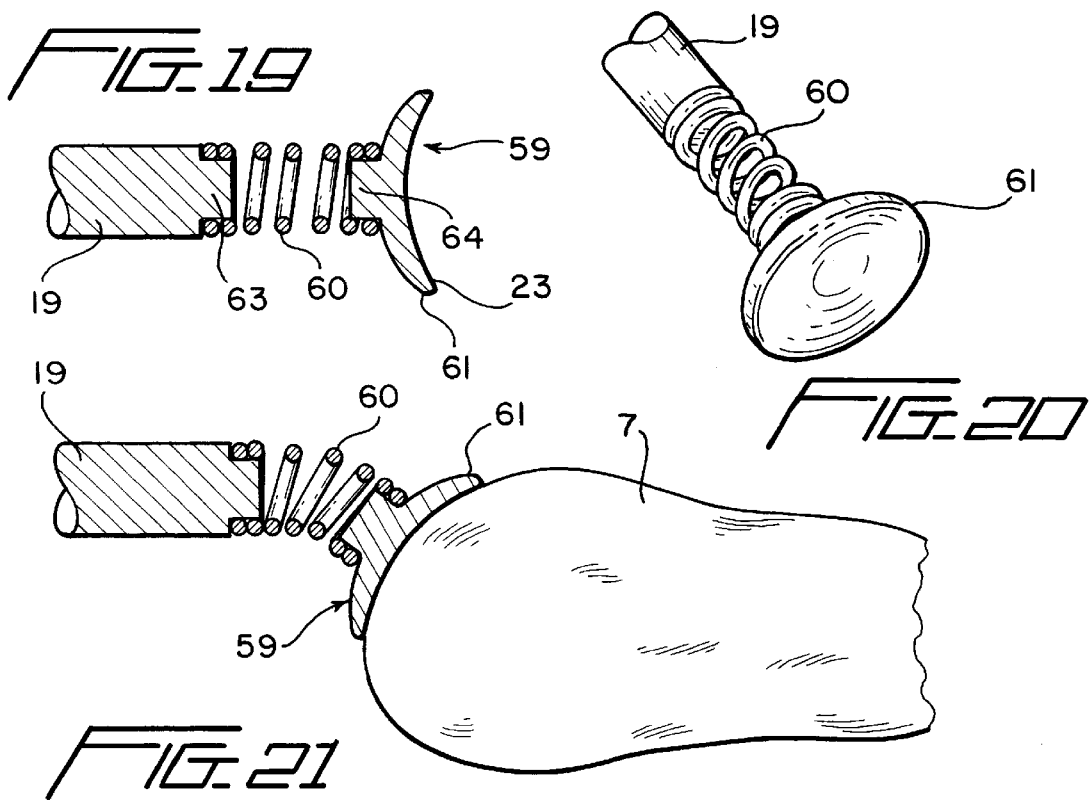

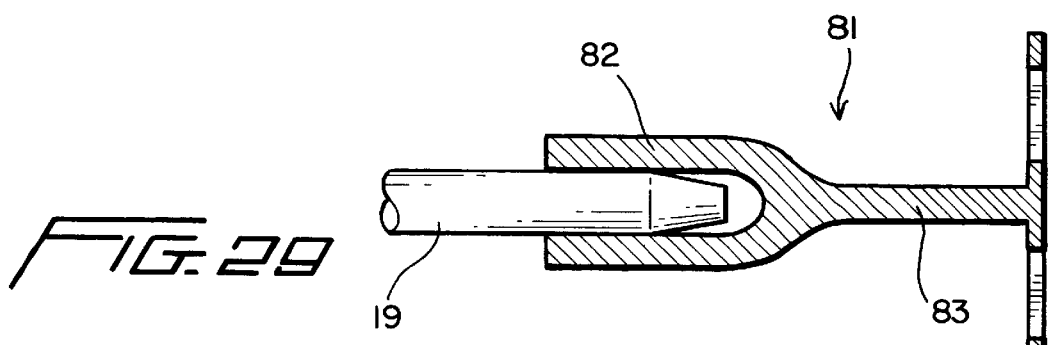
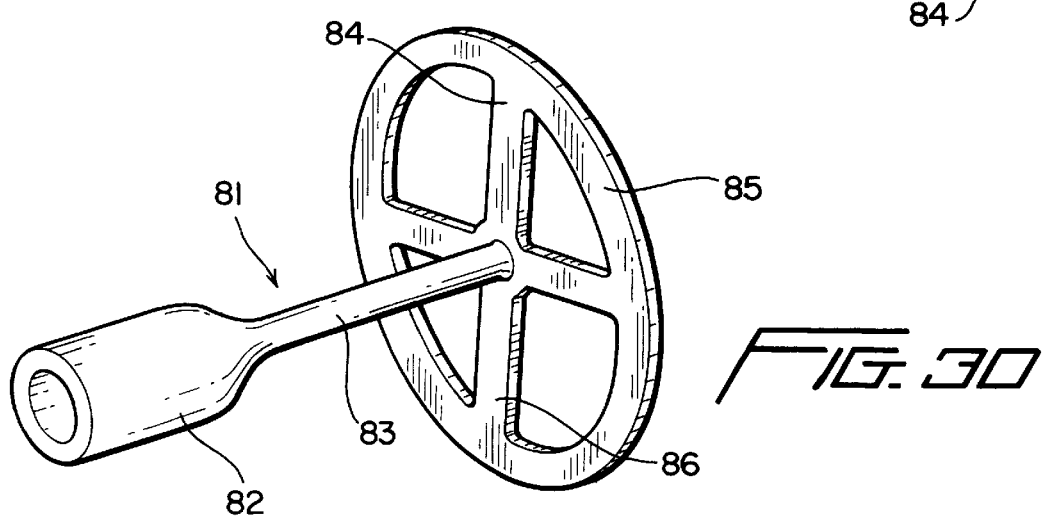
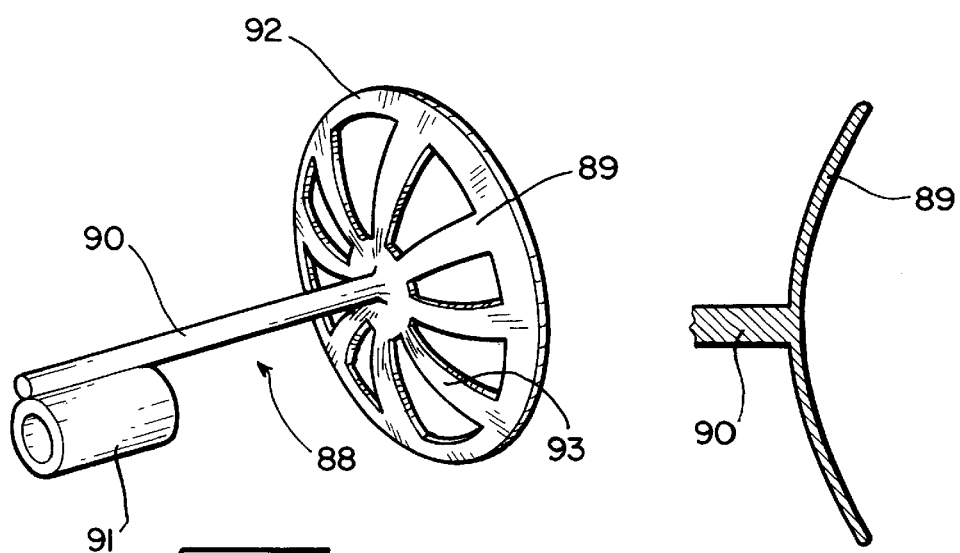

DEVICE FOR MECHANICAL COUPLING OF AN ELECTROMECHANICAL HEARING AID CONVERTER WHICH CAN BE IMPLANTED IN A MASTOID CAVITY

BACKGROUND OF THE INVENTION

1. Field of the Invention

The invention relates to a device for mechanical coupling of an output-side converter part of an electromechanical hearing aid converter which can be implanted in an artificial mastoid cavity outside the region of the middle ear, the converter part having a capacity to be excited to mechanical vibrations, to a preselected coupling site on the ossicular chain, the footplate of the stapes or the membrane which closes the round window or an artificial window in the cochlea, in the vestibulum or in the labyrinth (equilibrium organ), with a biocompatible, mechanically passive coupling arrangement which is connected to the output-side converter part and which reaches in the implanted state from the mastoid cavity into the tympanic cavity and adjoins the coupling site with the coupling end which is away from the hearing aid converter.

2. Description of Related Art

Electronic measures for rehabilitation of inner ear damage which cannot be surgically corrected have attained an important position today. With total failure of the inner ear, cochlear implants with direct electrical stimulation of the remaining auditory nerves are routinely used in clinical practice. In moderate to severe inner ear damage, for the first time fully digital hearing aids are being used which open a new world of electronic audio signal processing and offer expanded possibilities of deliberate precision audiological matching of the hearing aids to the individual inner ear damage. In spite of the major improvements in hearing aid hardware which have been achieved in recent years, in conventional hearing aids fundamental defects remain; they are due to the principle of acoustic amplification, i.e., especially to the conversion of the electronically amplified signal back into airborne sound. These defects include aspects such as the visibility of the hearing aids, poor sound quality as a result of the electromagnetic converters (speakers), the closed external auditory passage and feedback effects with high acoustic amplification.

As a result of these fundamental defects, there has long been the desire to abandon conventional hearing aids with acoustic excitation of the damaged inner ear and to replace these devices by partially implantable or fully implantable hearing systems with direct mechanical stimulation. Implantable hearing systems differ from conventional hearing aids; admittedly, the acoustic signal is converted into an electrical signal with a converter (microphone) and is amplified in an electronic signal processing stage; this amplified electrical signal is however not supplied to an electroacoustic converter, but to an implanted electromechanical converter which produces output-side mechanical vibrations which are supplied directly, therefore with direct mechanical contact, to the middle ear or inner ear or indirectly by a force-fit via an air gap in electromagnetic converter systems, for example. This principle applies regardless of whether there has been a partial or complete implantation of all necessary system components and also regardless of whether pure labyrinthine deafness is to be rehabilitated with a completely intact middle ear or a combined deafness (middle ear and inner ear damaged). Therefore, in the more recent scientific literature and in numerous patents, implantable electromechanical converters and processes for direct coupling of the mechanical converter vibrations to the intact middle ear or to the inner ear for rehabilitation of pure labyrinthine deafness and also to the remaining ossicles of the middle ear in an artificially or pathologically altered middle ear for care of conductive deafness and their combinations have been described.

Basically, all physical conversion principles can be used as electromechanical converter processes, i.e., electromagnetic, electrodynamic, magnetostrictive, dielectric, and piezoelectric. In recent years, various research groups have focused essentially on two of these processes; electromagnetic and piezoelectric. An outline of these converter versions can be found in Zenner and Leysieffer (HNO 1997 Vol. 45, 749–774).

In the piezoelectric process, mechanically direct coupling of the output-side converter vibrations to the middle ear ossicle or directly to the oval window is necessary. In the electromagnetic principle, the force coupling can take place via an air gap ("contactless"), i.e., only one permanent magnet is placed by permanent fixation in direct mechanical contact with a middle ear ossicle On the other hand, it is possible to execute the converter entirely within a housing (the coil and the magnet being coupled with the smallest possible air gap) and to transfer the output-side vibrations via a mechanically stiff coupling element with direct contact to the middle ear ossicle (Leysieffer et al. 1997 (HNO 1997, Vol. 45. pp. 792–800).

The patent literature contains some of the aforementioned versions of both electromagnetic and also piezoelectric hearing aid converters: U.S. Pat. No. 5,707,338 (Adams et al.), WO 98/06235 (Adams et al.), WO 98/06238 (Adams et al.), WO 98/06236 (Kroll et al.), WO 98/06237 (Bushek et al.), U.S. Pat. No. 5,554,096 (Ball), U.S. Pat. No. 3,712,962 (Epley), U.S. Pat. No. 3,870,832 (Fredrickson), U.S. Pat. No. 5,277,694 (Leysieffer et al.), commonly owned U.S. patent application Ser. Nos. 09/275,872 and 09/311,563 (Leysieffer), U.S. Pat. No. 5,015,224 (Maniglia), U.S. Pat. No. 3,882,285 (Nunley), and U.S. Pat. No. 4,850,962 (Schaefer).

The partially implantable piezoelectric hearing system of the Japanese group Suzuki and Yanigahara presupposes for implantation of the converter the absence of the middle ear ossicles and a free tympanic cavity in order to be able to couple the piezoelement to the stapes (Yanigahara et al.: Efficacy of the partially implantable middle ear implant in middle and inner ear disorders. Adv. Audiol., Vol. 4, Karger Basel (1988), pp. 149–159; Suzuki et al.: Implantation of partially implantable middle ear implant and the indication. Adv. Audiol., Vol. 4, Karger Basel (1998), pp. 160–166). Likewise, in the process of a partially implantable hearing system for those suffering from labyrinthine deafness of U.S. Pat. No. 4,850,962 (Schaefer), basically, the incus is removed in order to be able to couple a piezoelectric converter element to the stapes. This also applies especially to other developments which are based on Schaefer technology and which are documented in the aforementioned patents (U.S. Pat. No. 5,707,338, WO 98/06235, WO 98/06238, WO 98/06236, and WO 98/06237).

The electromagnetic converter of Ball ("Floating Mass Transducer FMT", U.S. Pat. No. 5,624,376 and U.S. Pat. No. 5,554,096) is conversely fixed with titanium clips directly on the long process of the incus when the middle ear is intact. The electromagnetic converter of the partially implantable system of FREDRICKSON (Fredrickson et al.: Ongoing investigations into an implantable electromagnetic hearing aid for moderate to severe sensorineural hearing loss. Otolaryngologic Clinics of North America, Vol. 28/1 (1995), pp. 107–121) is mechanically coupled directly to the body of the incus when the ossicular chain of the middle ear is likewise intact. The same applies to the piezoelectric and electromagnetic converters of LEYSIEFFER (Leysieffer et al.: An implantable piezoelectric hearing aid converter for patients with labyrinthine deafness. HNO 1997/45, pp. 792–800, U.S. Pat. No. 5,277,694, U.S. patent application Ser. No. 09/275,872, and U.S. patent application Ser. No. 09/311,563). Also in the electromagnetic converter system of MANIGLIA (Maniglia et al: Contactless semi-implantable electromagnetic middle ear device for the treatment of sensorineural hearing loss, Otolaryngologic Clinics of North America, Vol. 28/1 (1995), pp. 121–141) when the ossicular chain is intact a permanent magnet is permanently fixed mechanically to the ossicular chain and is however mechanically driven via an air gap coupling by a coil.

In the described converter and coupling versions basically two implantation principles can be distinguished:

a) In the case of the one principle the electromechanical converter with its active converter element is located itself in the middle ear region in the tympanic cavity and the converter is directly connected there to an ossicle or the inner ear (U.S. Pat. No. 4,850,962, U.S. Pat. No. 5,015,225, U.S. Pat. No. 5,707,338, WO 98/06235, WO 98/06238, WO 98/06236, WO 98/06237, U.S. Pat. No. 5,624,376, U.S. Pat. No. 5,554,096).

b) In the other principle the electromechanical converter with its active converter element is located outside of the middle ear region in an artificially formed mastoid cavity. The output-side mechanical vibrations are then transmitted to the middle or inner ear (Fredrickson et al.: Ongoing investigations into an implantable electromagnetic hearing aid for moderate to sever sensorineural hearing loss. Otolaryngologic Clinics of North America, Vol. 28/1 (1995), pp. 107–121; U.S. Pat. No. 5,277,694; U.S. patent application Ser. Nos. 09/275,872 and 09/311,563) by means of mechanically passive coupling elements via suitable surgical accesses (natural aditus ad antrum, opening of the chorda-facialis angle or via an artificial hole from the mastoid).

In version a), the converter can be made as a so-called "floating mass" converter, i.e., the converter elements does not require any "reaction" via secure screwing to the skull bone, but it vibrates based on the laws of mass inertia with its converter housing and transmits this directly to a middle ear ossicle (U.S. Pat. No. 5,624,376, U.S. Pat. No. 5,554,096, U.S. Pat. No. 5,707,338, WO 98/06236). On the one hand, this means that an implantable fixation system on the cranial vault can be advantageously omitted, and on the other hand, this version disadvantageously means that bulky artificial elements must be placed in the tympanic cavity and their long term stability and bio-stability are currently not known or guaranteed especially in the case of temporary pathological changes of the middle ear (for example, otitis media). One major disadvantage lies in that the converter is moved out of the mastoid with its electrical supply line into the middle ear and must be fixed there using suitable surgical tools; this requires expanded access through the chorda facialis angle and thus entails a latent hazard to the facial nerve which is located in the immediate vicinity.

In the converter versions as per b), the converter housing with the implantable positioning and fixation systems must be attached to the cranial vault (advantageous embodiment published German Patent Application 196 18 964 corresponding to U.S. Pat. No. 5,788,711). One disadvantage of the versions as per b) is that a depression must be made in the target ossicle in order to be able to apply the coupling element. This, on the one hand, is technically complex and expensive and, on the other hand, entails risks to the patient. Both in the partially implantable system of FREDRICKSON (Ongoing investigations into an implantable electromagnetic hearing aid for moderate to severe sensorineural hearing loss, Otolaryngologic Clinics of North America, Vol. 28/1 (1995), pp. 107–121) as well as in the fully implantable hearing system of LEYSIEFFER and ZENNER (HNO 1998, vol. 46, 853–863 and 844–852), when the vibrating converter part is coupled to the body of the incus it is assumed for permanent and mechanically secure vibration transmission that the tip of the coupling rod which is placed in the laser-induced depression of the middle ear ossicle undergoes osseointegration over the long term, i.e., the coupling rod coalesces solidly with the ossicle, and thus, ensures reliable transmission of dynamic compressive and tensile forces. However, this long-term effect is currently not yet scientifically proven or certain. Furthermore, in this type of coupling, in case of a technical converter defect, there is the disadvantage that decoupling from the ossicle to remove the converter can only be done with mechanically based surgical methods; this can mean considerable hazard to the middle ear and especially the inner ear.

The major advantage of these converter embodiments as per b), however, is that the middle ear remains largely free and coupling access to the middle ear can take place without major possible hazard to the facial nerve. One preferable surgical process for this purpose is described in U.S. patent application Ser. No. 09/168,079. Basic advantageous forms of passive coupling elements for transmission of the output-side converter vibrations from the mastoid to the middle ear or inner ear are described in published European Patent Applications EP-A 0 499 940 (corresponding to U.S. Pat. No. 5,277,964), and EP-A 0 901 779 (corresponding to U.S. patent application Ser. No. 09/042,805) and in HNO 1998 Vol. 46, 27–37, Lehner et al.: "Cold-flowing elements for coupling of an implantable hearing aid converter to the auditory ossicle or perilymph." They are especially coupling elements of gold, preferably soft-annealed fine gold, in the form of a C-band for the long process of the incus, a band loop for the long process of the incus and a tiny bell for the head of the stapes, and these coupling elements can be coupled using instruments which are standard in ear surgery, and if necessary, they can also be detached again.

In an external (not implantable) hearing aid with an electromagnetic output converter (EP-B-0 556 300), keeping a permanent magnet of the output converter on the outer surface of the eardrum by means of manually detachable surface adhesion by non-invasive means is known. But in this case, problems such as a non-optimum form of vibration of the footplate of the stapes by restraint of the ossicle and risky work in the inner ear during implantation do not play a role. In addition the large area which is available on the outside surface of the eardrum is not comparable to the tiny coupling surfaces in the middle ear.

In addition, a passive ossicle prosthesis with a head, a shaft and a flexible intermediate piece is known (WO 90/11737). The intermediate piece makes it possible to adjust the angular alignment of the shaft with reference to the head. In the implanted prosthesis the shaft is supported on the arch of the stapes, one leg of the stapes or the footplate of the stapes, while the prosthesis head adjoins the eardrum or the malleus under prestress such that the eardrum is slightly tensioned. The compressive force which is exerted on the prosthesis by the eardrum as a result keeps the prosthesis in place The head and the shaft of the prosthesis are preferably made of hydroxyl apatite or a mixture of hydroxyl apatite particles and silicone or polyurethane. Human tissue adheres to this material, by which fixing of the prosthesis in the middle ear is to be supported.

SUMMARY OF THE INVENTION

The object of this invention is to devise a device for coupling of the hearing aid converter and for transmission of the output-side converter vibrations to the middle ear or inner ear, which can be applied more easily and reliably while preserving the aforementioned advantages of version b), which minimizes the necessary risky effort during implantation in the inner ear, which also facilitates decoupling which becomes necessary later under certain circumstances and which promotes an optimum form of vibration of the footplate of the stapes.

Proceeding from a device of the type which is known from U.S. Pat. No. 5,941,814 and HNO Vol. 46, 27–37, i.e., a device for mechanical coupling of an output-side converter part of an electromechanical hearing aid converter which can be implanted in an artificial mastoid cavity outside the region of the middle ear, the converter part having a capacity to be excited to mechanical vibrations, to a preselected coupling site on the ossicular chain, the footplate of the stapes or the membrane which closes the round window or an artificial window in the cochlea, in the vestibulum or in the labyrinth (equilibrium organ), with a biocompatible mechanically passive coupling arrangement which is connected to the output-side converter part and which reaches in the implanted state from the mastoid cavity into the tympanic cavity and adjoins the coupling site with the coupling end which is away from the hearing aid converter, this object is achieved in accordance with the present invention by forming the coupling end of a coupling element with a contact surface which has a surface shape which is matched or which can be matched to the surface shape of the coupling site and has a surface composition and surface size such that, by placing the coupling end against the coupling site, dynamic tension-compression force coupling of the coupling element and the preselcted coupling site occurs by surface adhesion which is sufficient for reliable mutual connection of the coupling element and the coupling site.

The device according to the invention provides for coupling of the output-side converter part of an electromechanical hearing aid converter which can be implanted in a mastoid cavity to an ossicle (malleus, incus, stapes; preferably the incus), to the footplate of the stapes or to a membrane which closes the round window or an artificial window by surface adhesion. Here the expression "surface adhesion" means adhesion under the influence of the molecular forces of attraction which take effect with a sufficiently close approach to the contact surfaces, or mutual mechanical interlocking of the contact surfaces without using an adhesive or cement. Air bubbles which are enclosed in the surface depressions can also contribute to corresponding surface adhesion. If the contact surfaces are exposed to forces which seek to separate the surfaces these air bubbles produce a suction effect; this makes separation very difficult (Bild der Wissenschaft, April 1999, p, 10).

One basic advantage of this adhesion coupling is that the coupling site, for example, of the ossicle is not "restrained" primarily in the direction of vibration of the driving converter, and this "restraint" can lead to a non-optimum form of vibration of the footplate of the stapes in the oval window. (One preferable form of vibration is a piston-like vibration of the footplate of the stapes perpendicular to its plane). Rather, the ossicle adjusts its (frequency-dependent) vibration direction due to the dynamic properties of the intact middle ear itself when surface adhesion coupling is being used. This advantage also applies for a non-intact (partially) decomposed ossicular chain and coupling to the remainder of the chain facing the inner ear, and in the extreme case, also for only residual stapes or only the footplate of the stapes since it is suspended by the so-called ligament (an elastic annular band which "holds" the stapes in the oval window). In addition, there is postoperative detachability of the ossicle coupling even after years in the body. This approach to connection is possible with reasonable expenditure of force and using instruments which are standard in ear surgery.

In particular, the coupling arrangement feasibly has a coupling rod which reaches in the implanted state from the mastoid cavity into the tympanic cavity and which is securely joined to the output-side converter part and has a coupling element which is connected or can be connected to the end of the coupling rod away from the output-side converter part and forms the coupling end of the coupling arrangement. This coupling rod represents a mechanically stiff coupling element of comparatively small mass which can be securely attached to the outside of a vibratory membrane of the electromechanical hearing aid converter and which can be pushed into the middle ear from the mastoid when implanted through the natural or artificially, slightly widened aditus ad antrum, through an opening of the chorda facialis angle or through an artificial hole in order to be connected there via the coupling element to the desired coupling site. It is thus guaranteed that the vibratory stimulus of the converter is introduced into the coupling site, such as a target ossicle, largely without losses.

The coupling rod and the coupling element can be Joined to one another via a flexible intermediate element which can be a separate component or which can be formed by the coupling element itself In the latter case, the coupling element can be provided easily with a constriction for purposes of forming the flexible intermediate element. The flexible intermediate element can be optimally adjusted automatically with respect to its solid angle or can be individually plastically adjusted in the optimum manner by the surgeon during the surgery.

The flexible intermediate element can advantageously be made as a spring element and can be made of a metal alloy with memory effect or so-called "superelasticity," especially nitinol. The use of this material has the advantage that the transmitted force also remains roughly the same at different adjustment distances.

The coupling rod and the coupling element can, however, also be connected to one another via a ball joint in order to achieve the above described optimum solid angle adjustment. Preferably the coupling arrangement is made and/or positioned in the implanted state such that the coupling end touches the coupling site without static prestress or with only slight prestress. This contributes to a reliable bond by surface adhesion when, at least in the implanted state, a film of moisture is formed between the coupling end and the coupling site. To do this, a natural film of moisture can be used which can be attributed to the 100% moisture which is present in the middle ear space.

The coupling end can advantageously be made concave before coupling with reference to the coupling site. In this way, when the coupling end is applied to the coupling site, a cavity is formed which is pressed together by slightly pressing against the coupling end. The negative pressure which has formed here supports adhesion.

The coupling site can also be formed by a coupling plate which can optionally be anatomically matched and which in the implanted state is securely joined, for example, cemented, to the surface of the part of the ossicular chain with which contact is to be made, the footplate of the stapes or a membrane which closes the round window or an artificial window. In this way, provisions can be made for an even better defined adhesion action because dynamic force transmission takes place between two defined materials and geometries which can be optimized for adhesion coupling. Coupling is then also more reproducible in its action than in direct action on an ossicle.

Improved anatomic adjustment possibilities can be achieved under certain circumstances by the coupling element having a large-area, open structure on the coupling end and/or being provided with several elastic arms.

These and further objects, features and advantages of the present invention will become apparent from the following description when taken in connection with the accompanying drawings which, for purposes of illustration only, show several embodiments in accordance with the present invention.

BRIEF DESCRIPTION OF THE DRAWINGS

FIGS. 4 and 5, respectively, are a perspective view and a sectional view similar to those of FIGS. 2 and 3, but showing a modified embodiment of the coupling arrangement;

FIGS. 6 and 7, respectively, are a perspective view and a sectional view similar to those of FIGS. 2 and 3, but showing another modified embodiment of the coupling arrangement;

FIGS. 8 and 9, respectively, are a perspective view and a sectional view similar to those of FIGS. 2 and 3, but showing yet another modified embodiment of the coupling arrangement;

FIG. 10 is a partial side view of the coupling arrangement as shown in FIGS. 8 and 9 positioned adjacent to the incus body;

FIG. 11 shows a section of a coupling arrangement with a two-part coupling element;

FIGS. 12 and 13, respectively, are a perspective view and a sectional view similar to those of FIGS. 2 and 3, but showing a further embodiment of the coupling arrangement;

FIG. 14 is a partial sectional view showing the coupling arrangement of FIGS. 12 and 13 adjacent to the incus body;

FIGS. 15 and 16, respectively, are a perspective view and a sectional view similar to those of FIGS. 2 and 3, but showing another modified embodiment of the coupling arrangement;

FIG. 17 is a perspective representation of the coupling arrangement of FIGS. 15 and 16 with an intermediate element which is bent in the course of implantation;

FIG. 18 is a partial sectional view of the coupling arrangement of FIGS. 15 to 17 adjacent to the incus body;

FIGS. 19 and 20, respectively, are a perspective view and a sectional view similar to those of FIGS. 2 and 3, but showing a further modified embodiment of the coupling arrangement;

FIG. 21 is a partial sectional view of the coupling arrangement of FIGS. 19 and 20 adjacent to the incus body;

FIGS. 29 and 30, respectively, are a perspective view and a sectional view, similar to those of FIGS. 2 and 3, of still another modified embodiment of the coupling arrangement;

FIGS. 31 and 32, respectively, are a perspective view and a sectional view similar to those of FIGS. 2 and 3, but showing another modified embodiment of the coupling arrangement;

DETAILED DESCRIPTION OF THE INVENTION

Figure 1:
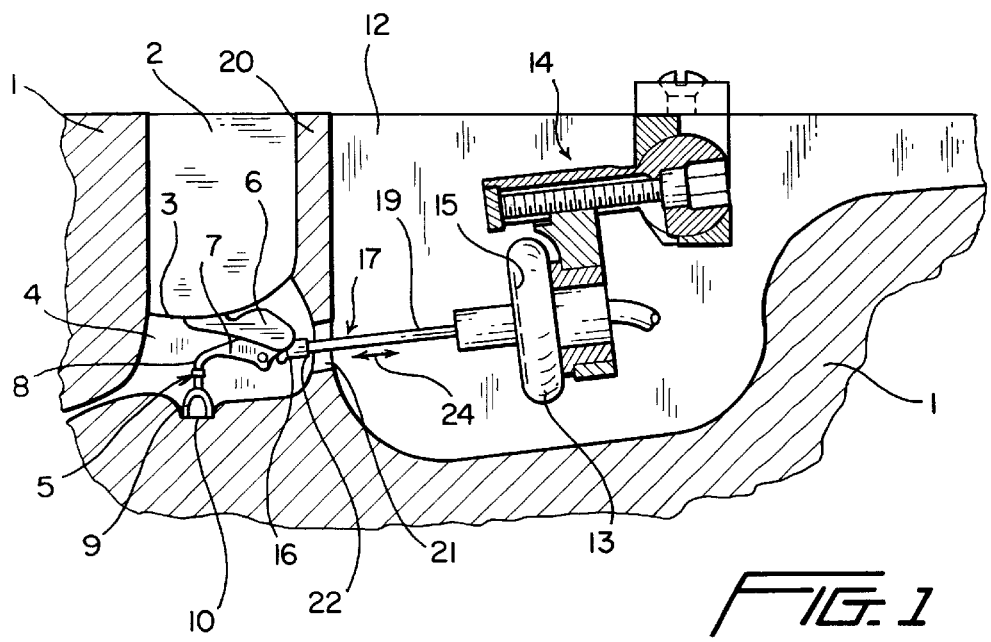
FIG. 1 is a sectional view of part of the human skull with an implanted electromechanical hearing aid converter and a preferred embodiment of the device for mechanical coupling of the output-side converter part to the ossicular chain.

FIG. 1 shows part of a human skull bone 1 with the auditory passage, the middle ear space (tympanic cavity) 4 which is separated from it by the eardrum 3, and the ossicular chain 5 which is located in the tympanic cavity, to which the malleus 6, the incus 7 with the incus process 8 and the stapes (stirrup) 9 with the footplate 10 of the stapes belong. An electromechanical hearing aid converter 13 is fixed by means of a positioning and fixing system 14 in an artificial mastoid cavity 12. The hearing aid converter 13 can be built, for example, as a piezoconverter for vibratory stimulation of the ossicular chain, especially in the manner known from U.S. Pat. No. 5,277,694 and it is a component of at least one partially implantable and preferably fully implantable hearing aid, for example, a hearing aid of the type known from HNO 1997 Vol. 45, 749–774.

For mechanical coupling of an output-side converter part 15 of the hearing aid converter 13, which is shown only schematically in FIG. 1 and which can be excited to mechanical vibrations to a preselected coupling side 16 on the ossicular chain 5, for example, to the "smooth" body of the incus 7, from the mastoid side, there is a biocompatible mechanically passive coupling arrangement 17 which is connected to the actively vibrational output-side converter 15 part and which, in the implanted state, adjoins the coupling site 16 with the coupling end 18 which is away from the hearing aid converter 13. When an electrical voltage is applied to the hearing aid converter 13, the coupling arrangement 17 is caused to execute vibratory oscillations in the axial direction of the coupling arrangement by means of the output-side converter part 15. As a result, the electrically converted audio signals, which are picked up by an unillustrated input side converter (microphone) after electronic amplification in an electronic module of the hearing aid, lead directly to mechanical deflections of the coupling arrangement 17. These deflections correspond to the acoustic information. The deflections of the coupling arrangement 17 are relayed to the ossicularchain of the middle ear or to the stapes or the oval or round window. Therefore, these deflections cause an audiological amplification effect in a corresponding design of the preprocessing electronic system.

The coupling arrangement 17 in this embodiment has a coupling rod 19 which is mechanically joined securely to the output-side converter part 15, which in this embodiment has essentially over its entire length the shape of a straight cylinder and which extends in the implanted state from the mastoid cavity 12 into the tympanic cavity 4 through a natural bone opening (aditus ad antrum) 21 which is located in the rear wall 20 of the auditory passage. Furthermore, the coupling arrangement 17 includes a coupling element 22 which is connected to the end of the coupling rod 19 away from the hearing aid converter 13 and forms the coupling end 18 of the coupling arrangement 17. The coupling end 18 has a contact surface 23 which has a surface shape which is matched to the surface shape of the coupling site 16 and has a surface composition and surface size such that, by placing the coupling end 18 against the coupling site 16, dynamic tension-compression force coupling of the coupling element 22 and the target ossicle (the incus 7 in this case) occurs by surface adhesion which is sufficient for mutual connection of the coupling element 22 and the ossicular chain 5 without play. The adhesion action here is supported by the circumstance that the middle ear space 4 always has 100% humidity, and as a result, there is a natural film of moisture on the ossicles 6, 7, 9. The coupling element 22, in its basic form, is made according to the target ossicle or the local part of the target ossicle on the coupling site 16 (concave, convex or planar), such that the coupling element touches the ossicle without static prestress, or with a slight prestress, and causes dynamic tension-compression force coupling as a result of the adhesion which arises. The desired static prestress relative to the suspensory ligaments of the middle ear can be produced by the deliberate advance of the converter 13, and thus, the coupling rod 19, corresponding to the double arrow 24 in FIG. 1, by means of the positioning and fixing system 14. Positioning and fixing systems which are suitable for this purpose are described in U.S. Pat. No. 5,788,711 and in the older U.S. patent application Ser. No. 09/468,853, which are hereby incorporated by reference.

Figure 2:
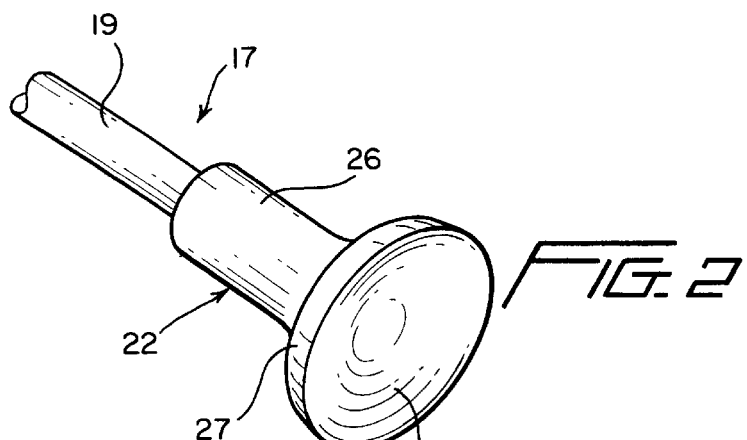
FIG. 2 an enlarged perspective representation of the coupling element and part of the coupling rod of the coupling arrangement as shown in FIG. 1.
Figure 3:
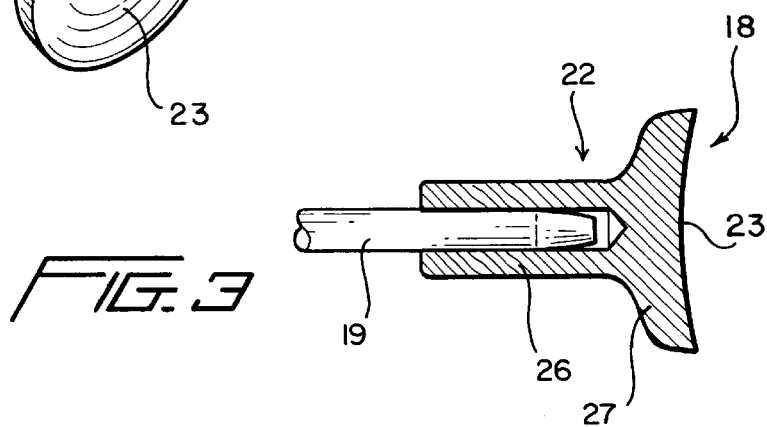
FIG. 3 shows a section of the coupling arrangement as shown in FIG. 2.

The coupling element 22 which is shown in FIGS. 2 and 3 on a larger scale has a sleeve-shaped section 26 and a flange section 27 which represents the coupling end 18 of the coupling arrangement 17, which is joined in one piece to the sleeve-shaped section, and which is provided with a concave contact surface 23. The sleeve-shaped section 26 of the coupling element 22 is pushed onto the end of the coupling rod 19 which is away from the converter 13 and is securely joined to the coupling rod, for example, crimped, welded, soldered or also cemented.

FIGS. 4 and 5 show a coupling element 29 which differs from the coupling element 22 only in that the sleeve-shaped section 30 adjoins a spherical head 31 which forms the coupling end. The head 31 has a larger diameter than the section 30 and it has a convexly curved contact surface 32.

FIGS. 6 and 7 show a coupling element 34 which has been slipped onto the free end of the coupling rod 19 with an essentially constant outside diameter and hemispherical coupling end 35.

The coupling element 37 which is shown in FIGS. 8–10 is similar to the coupling element 22 of FIGS. 2 and 3. In addition however, the coupling element 37 has a flexible intermediate element in the form of a constriction 38 at a transition site between the sleeve-shaped section 26 and the flange section 27. Depending on the material chosen for the coupling element in the particular case and the dimensioning of the constriction 38, the angle of the contact surface 23 can thus be automatically adjusted optimally relative to the coupling site 16, or the coupling element can be individually plastically deformed in an optimum manner by the surgeon during the surgery.

In the embodiment of FIG. 11, a coupling element 40 has a relatively large-area flange section 41 with a concave contact surface 23. The concave contact surface 23 faces a surface 42 of a thin coupling plate 43, a surface which is convexly curved in a complementary manner and which, in this example, is securely joined to the surface of the incus body 7. The coupling plate 43 can, if necessary, be anatomically adapted. Between the surfaces 23 and 42 there is preferably a liquid film 44. This arrangement makes it possible to achieve an even better defined and better reproducible adhesion action than with direct action on an ossicle because dynamic force transmission takes place between two defined materials and geometries. In this embodiment, the coupling element 40 is bluntly joined to the coupling rod 19. Instead, the free end of the coupling rod can also be accommodated by a sleeve-shaped section which adjoins the flange section 41 according to FIGS. 5, 7 and 9.

The adjustment of the contact surface which is explained in conjunction with the embodiment of FIGS. 8 to 10 can be achieved by a pivot element as shown in FIGS. 12 to 14. In this case, there is a coupling element 46 in which a ball receiver 47 adjoins the flange section 27 which forms the contact surface 23. A spherical head 48 which is part of a ball joint part 49 is permanently joined to the coupling rod 19 and fits into the ball receiver 47. The ball joint 50, which is comprised of the ball receiver 47 and the ball joint part 49, not only allows adjustment of the angle of the contact surface 23 with reference to the longitudinal axis of the coupling, rod 19, but in addition also rotation of the coupling rod 19 relative to the coupling element 46. It goes without saying that, in contrast to the embodiment shown, the ball joint part which is securely joined to the coupling rod 19 can be made as a ball receiver which interacts with a ball head which is part of the coupling element. Furthermore, optionally, a special intermediate part between the coupling rod and the coupling element can be eliminated by the spherical head or the ball receiver being molded directly onto the coupling rod.

FIGS. 15 to 18 show an embodiment in which a flexible intermediate element 53, in the form of a separate component, is inserted between the coupling rod 19 and a coupling element 52 in order to be able to adjust the angle of the contact surface 23. The coupling element 52 has a relatively large-area flange section 54 with a connecting piece 55 which projects from the surface of the coupling element 52 which is opposite the contact surface 23. The free end of the connecting piece 55 is slightly crowned and fits into a complementary recess 56 on one end of the intermediate element 53. Correspondingly, the other end of the intermediate element 53 is joined to the coupling rod 19.

Figure 22:
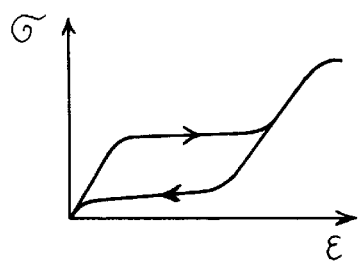
FIG. 22 is a stress-strain diagram of the spring material (nitinol) which can be provided preferably in the coupling arrangement of FIGS. 19 to 21, FIGS. 23 and 24, respectively, are a perspective view and a sectional view similar to those of FIGS. 2 and 3, but showing yet another modified embodiment of the coupling arrangement.

In the case of the embodiment of the coupling element 59 as shown in FIGS. 19 to 21, there is a helical spring 60 which joins a flange section 61 of the coupling element 59 to the coupling rod 19 that serves as a flexible intermediate element. The ends of the helical spring 60 are joined at least by force-fit to the spring supports 63 and 64 of the coupling rod 19 and flange section 61. The spring 60 can, optionally, be produced from a metal alloy with a memory effect, especially nitinol. One such metal alloy can also be characterized by so-called "superelasticity," i.e., the transmitted force remains, as follows from the stress-strain diagram of FIG. 22, roughly the same in a certain range even for different adjustment distances.

Other possible spring elements are shown in FIGS. 23 to 28.

Figure 23:
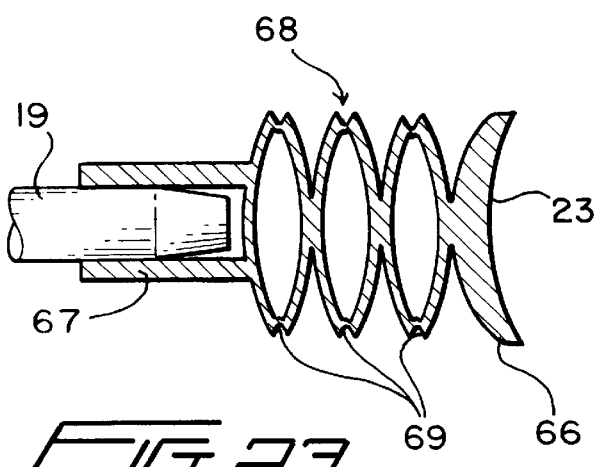
Figure 24:
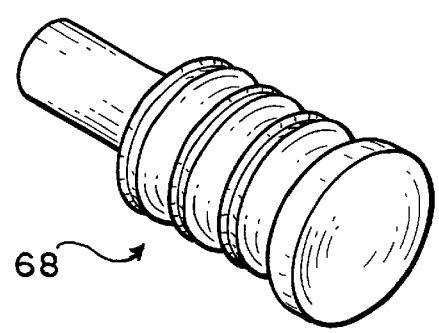

In the embodiment as shown in FIGS. 23 and 24, between a flange section 66 which forms the contact surface 23 and a sleeve-shaped section 67 of a coupling element 68, there are three disk spring sections 69.

Figure 25:
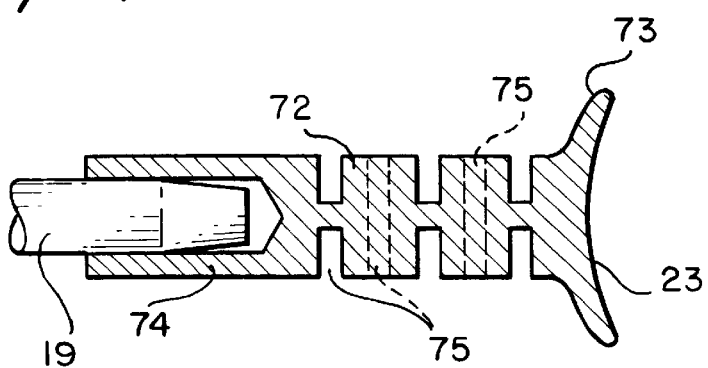
FIGS. 25 and 26, respectively, are a perspective view and a sectional view similar to those of FIGS. 2 and 3, but showing an additional modified embodiment of the coupling arrangement.
Figure 26:
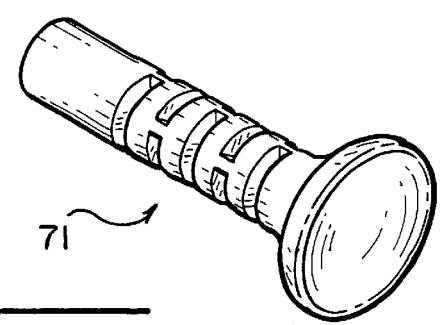

In the case of the embodiment which is shown in FIGS. 25 and 26, there is a coupling element 71 with a cylindrical section 72 which is inserted between a flange section 73 which forms the contact surface 23 and a sleeve-shaped section 74. In the cylindrical section 72, there is a series of notches 75 which are offset in the peripheral direction by 90°, by which spring properties are imparted to the cylindrical section 72.

Figure 27:
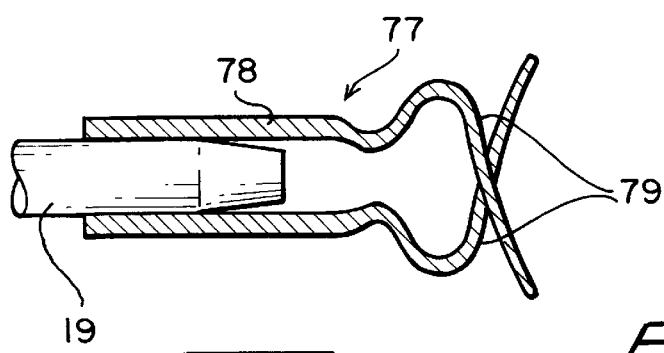
FIGS. 27 and 28, respectively, are a perspective view and a sectional view similar to those of FIGS. 2 and 3 for a further modified embodiment of the coupling arrangement.
Figure 28:
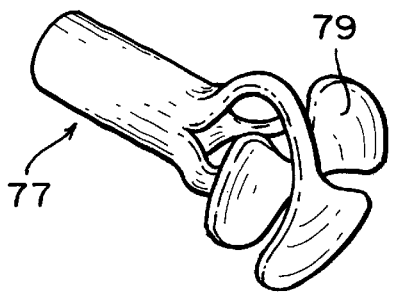

In the coupling element 77 as shown in FIGS. 27 and 28, the sleeve-shaped section 78 passes into an arrangement of three spring clips 79 which are offset in the peripheral direction relative to another.

The coupling element 81 which is shown in FIGS. 29 and 30 has a sleeve-shaped section 82 which is joined to a planar adhesion element 84 via a slender shaft 83 which is concentric to the section 82. The adhesion element 84 has an open structure with an outer ring 85 joined to a hub by a plurality of spokes 86. The coupling element 88 of the embodiment of FIGS. 31 and 32 is provided with an open concave adhesion element 89. The adhesion element 89 is connected via a shaft 90 with a sleeve-shaped section 91 which can be pushed onto the coupling rod and which is attached laterally to the shaft 90. The adhesion element 89 includes in turn an outer ring 92 and a plurality of spokes 93. The outer rings 85, 92 can likewise be open (slotted) for better anatomic adjustment potential in a manner which is not shown.

Figure 33:
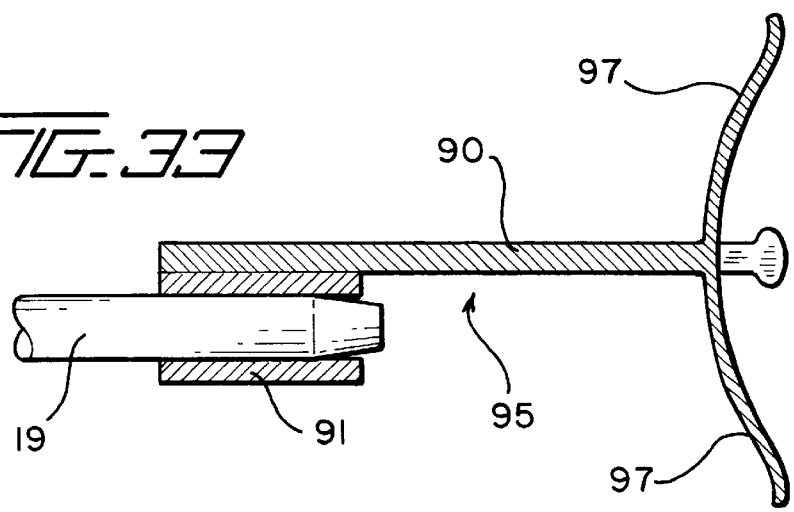
FIGS. 33 and 34, respectively, are a perspective view and a sectional view, similar to those of FIGS. 2 and 3, of yet another modified embodiment of the coupling arrangement.
Figure 34:
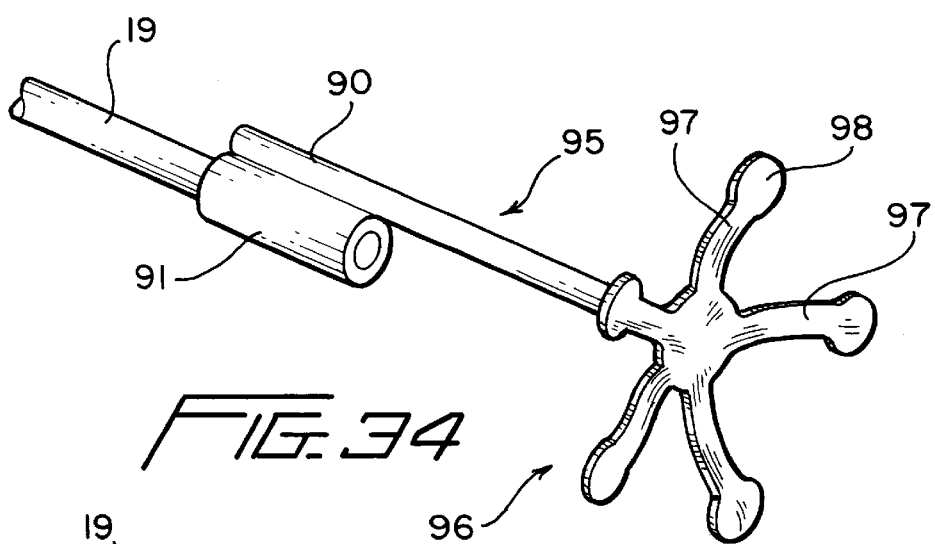
Figure 35:
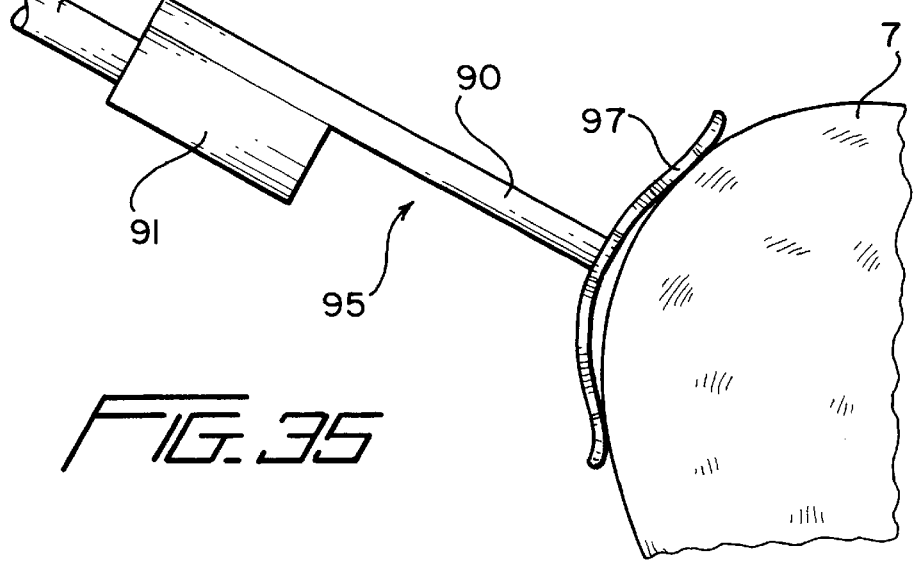
FIG. 35 is a side view of the coupling arrangement of FIGS. 33 and 34 adjacent to the incus body.

Entirely omitting the outside ring 85 or 92 yields a coupling element 95 of the type which is shown in FIGS. 33 to 35 in which an adhesion element 96 has a plurality of projecting arms 97. The free ends 98 of the arms 97 have a rounded pad-shape and together form the contact surface.

The described coupling arrangement can, basically, be formed of any biocompatible materials, especially metals, metal alloys and/or plastics. Metallic materials include mainly titanium, gold, silver, niobium, tantalum, platinum, platinum-iridium, or alloys of these metals, implant steel, NiTi (nitinol), or other biocompatible shape memory metals. The plastics can be mainly silicones, polyurethanes, PTFE, FEP, polycarbonates, and the like. This wide selection, especially of plastics, can be narrowed accordingly if special material properties, such as plastic deformability, are necessary for individual matching to the target ossicle.

In the choice of materials and the structural design it should be borne in mind that what matters is feeding the vibrational stimulus (action) of the converter 13 into the target ossicle with as little losses as possible, i.e, reverberatively. In doing so, the total mass of the coupling arrangement should preferably be less than the mass of the incus, which is 25 mg on average. A minimum possible weight of the coupling arrangement leads, moreover, to a reduction of the forces of inertia upon acceleration by external effects such as impact, vibration, and the like.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as are encompassed by the scope of the appended claims.

What is claimed is:

1. A device for mechanical coupling an output-side converter part of an electromechanical hearing aid converter, is implantable in an artificial mastoid cavity outside the region of the middle ear, the output-side converter part having a capacity to be excited to mechanical vibrations, to a preselected coupling site selected from the group consisting of a site on the ossicle chain, the footplate of the stapes or the membrane which closes the round window or an artificial window in the cochlea, in the vestibulum or in the labyrinth (equilibrium organ), said device comprising a biocompatible, mechanically passive coupling arrangement which, in use, is connected to the output-side converter part and reaches, in an implanted state, from the mastoid cavity into the tympanic cavity, said coupling arrangement having a coupling end which is remote from the hearing aid converter for joining to the coupling site, the coupling end having a contact surface with a surface shape which is matchable or is matched to a surface shape of the coupling site and has a surface composition and surface size which produces a dynamic tension-compression force coupling of the coupling end to the coupling site by surface adhesion which is sufficient for reliable mutual connection of the coupling end and the selected coupling site by placing the coupling end against the coupling site and without using an adhesive or cement.

2. Device as claimed in claim 1, wherein the coupling end is concave before coupling to the coupling site.

3. Device as claimed in claim 1, wherein the coupling site is formed by a coupling plate which in the implanted state is securely joined to the surface of the coupling site with which contact is to be made.

4. Device as claimed in claim 1, wherein the coupling element has a large-area, open structure on the coupling end.

5. Device as claimed in claim 1, wherein the coupling element is provided with a plurality of flexible arms on the coupling end.

6. A device for mechanical coupling an output-side converter part of an electromechanical hearing aid converter to a preselected coupling site selected from the group consisting of a site on the ossicle chain, the footplate of the stapes or the membrane which closes the round window or an artificial window in the cochlea, in the vestibulum or in the labyrinth (equilibrium organ), wherein the hearing aid converter is implantable in an artificial mastoid cavity outside the region of the middle ear, wherein the output-side converter part is adapted to be excited to mechanical vibrations, said device comprising:

a biocompatible, mechanically passive coupling arrangement which, in use, is connected to the output-side converter part and reaches, in an implanted state, from the mastoid cavity into the tympanic cavity, said coupling arrangement including:

a coupling rod which is securely joined to the output-side converter part and which, in the implanted state, is adapted to reach from the mastoid cavity into the tympanic cavity; and a coupling end for joining to the coupling site, the coupling end being connected via a ball joint to the end of the coupling rod remote from the output-side converter part, the coupling end having a contact surface with a surface shape which is matchable or is matched to a surface shape of the coupling site and has a surface composition and surface size which produces a dynamic tension-compression force coupling of the coupling end to the coupling site by surface adhesion which is sufficient for reliable mutual connection of the coupling end and the selected coupling site by placing the coupling end against the coupling site.

7. Device as claimed in claim 6, wherein the coupling rod and the coupling end are joined to one another via a flexible intermediate element.

8. Device as claimed in claim 7, wherein the flexible intermediate element is formed by a part of the coupling element itself.

9. Device as claimed in claim 8, wherein the flexible intermediate element is formed by a constriction of the coupling element.

10. Device as claimed in claim 7, wherein the flexible intermediate element is a separate component.

11. Device as claimed in claim 7, wherein the flexible intermediate element comprises a spring element.

12. Device as claimed in claim 11, wherein the flexible intermediate element is made of a metal alloy with memory effect.

13. Device as claimed in claim 12, wherein the metal alloy with a memory effect is nitinol.

14. A device for mechanical coupling an output-side converter part of an electromechanical hearing aid converter to a preselected coupling site selected from the group consisting of a site on the ossicle chain, the footplate of the stapes or the membrane which closes the round window or an artificial window in the cochlea, in the vestibulum or in the labyrinth (equilibrium organ), wherein the hearing aid converter is implantable in an artificial mastoid cavity outside the region of the middle ear, wherein the output-side converter part is adapted to be excited to mechanical vibrations, said device comprising:

a biocompatible, mechanically passive coupling arrangement which, in use, is connected to the output-side converter part and reaches, in an implanted state, from the mastoid cavity into the tympanic cavity, said coupling arrangement having a coupling end which is remote from the hearing aid converter for joining to the coupling site, the coupling end having a contact surface with a surface shape which is matchable or is matched to a surface shape of the coupling site and has a surface composition and surface size which produces a dynamic tension-compression force coupling of the coupling end to the coupling site by surface adhesion which is sufficient for reliable mutual connection of the coupling end and the selected coupling site by placing the coupling end against the coupling site, the coupling arrangement being made such that the coupling end touches the coupling site without static prestress.

15. A device for mechanical coupling an output-side converter part of an electromechanical hearing aid converter to a preselected coupling site selected from the group consisting of a site on the ossicle chain, the footplate of the stapes or the membrane which closes the round window or an artificial window in the cochlea, in the vestibulum or in the labyrinth (equilibrium organ), wherein the hearing aid converter is implantable in an artificial mastoid cavity outside the region of the middle ear, wherein the output-side converter part is adapted to be excited to mechanical vibrations, said device comprising:

a biocompatible, mechanically passive coupling arrangement which, in use, is connected to the output-side converter part and reaches, in an implanted state, from the mastoid cavity into the tympanic cavity, said coupling arrangement having a coupling end which is remote from the hearing aid converter for joining to the coupling site, the coupling end having a contact surface with a surface shape which is matchable or is matched to a surface shape of the coupling site and has a surface composition and surface size which produces a dynamic tension-compression force coupling of the coupling end to the coupling site by surface adhesion which is sufficient for reliable mutual connection of the coupling end and the selected coupling site by placing the coupling end against the coupling site, the coupling arrangement, in the implanted state, being positioned such that the coupling end touches the coupling site without static prestress.

16. A device for mechanical coupling an output-side converter part of an electromechanical hearing aid converter to a preselected coupling site selected from the group consisting of a site on the ossicle chain, the footplate of the stapes or the membrane which closes the round window or an artificial window in the cochlea, in the vestibulum or in the labyrinth (equilibrium organ), wherein the hearing aid converter is implantable in an artificial mastoid cavity outside the region of the middle ear, wherein the output-side converter part is adapted to be excited to mechanical vibrations, said device comprising:

a biocompatible, mechanically passive coupling arrangement which, in use, is connected to the output-side converter part and reaches, in an implanted state, from the mastoid cavity into the tympanic cavity, said coupling arrangement having a coupling end which is remote from the hearing aid converter for joining to the coupling site, the coupling end having a contact surface with a surface shape which is matchable or is matched to a surface shape of the coupling site and has a surface composition and surface size which produces a dynamic tension-compression force coupling of the coupling end to the coupling site by surface adhesion which is sufficient for reliable mutual connection of the coupling end and the selected coupling site by placing the coupling end against the coupling site, the coupling arrangement being made such that the coupling end touches the coupling site with static prestress.

17. A device for mechanical coupling an output-side converter part of an electromechanical hearing aid converter to a preselected coupling site selected from the group consisting of a site on the ossicle chain, the footplate of the stapes or the membrane which closes the round window or an artificial window in the cochlea, in the vestibulum or in the labyrinth (equilibrium organ), wherein the hearing aid converter is implantable in an artificial mastoid cavity outside the region of the middle ear, wherein the output-side converter part is adapted to be excited to mechanical vibrations, said device comprising:

a biocompatible, mechanically passive coupling arrangement which, in use, is connected to the output-side converter part and reaches, in an implanted state, from the mastoid cavity into the tympanic cavity, said coupling arrangement having a coupling end which is remote from the hearing aid converter for joining to the coupling site, the coupling end having a contact surface with a surface shape which is matchable or is matched to a surface shape of the coupling site and has a surface composition and surface size which produces a dynamic tension-compression force coupling of the coupling end to the coupling site by surface adhesion which is sufficient for reliable mutual connection of the coupling end and the selected coupling site by placing the coupling end against the coupling site, wherein the coupling arrangement, in the implanted state, is positioned such that the coupling end touches the coupling site with slight prestress.

18. A device for mechanical coupling an output-side converter part of an electromechanical hearing aid converter to a preselected coupling site selected from the group consisting of a site on the ossicle chain, the footplate of the stapes or the membrane which closes the round window or an artificial window in the cochlea, in the vestibulum or in the labyrinth (equilibrium organ), wherein the hearing aid converter is implantable in an artificial mastoid cavity outside the region of the middle ear, wherein the output-side converter part is adapted to be excited to mechanical vibrations, said device comprising:

a biocompatible, mechanically passive coupling arrangement which, in use, is connected to the output-side converter part and reaches, in an implanted state, from the mastoid cavity into the tympanic cavity, said coupling arrangement having a coupling end which is remote from the hearing aid converter for joining to the coupling site, the coupling end having a contact surface with a surface shape which is matchable or is matched to a surface shape of the coupling site and has a surface composition and surface size which produces a dynamic tension-compression force coupling of the coupling end to the coupling site by surface adhesion which is sufficient for reliable mutual connection of the coupling end and the selected coupling site by placing the coupling end against the coupling site, wherein a film of moisture is formed, at least in the implanted state, between the coupling end and the coupling site.

* * * * *